United States Patent [19]

Bonello et al.

[11] Patent Number: 4,734,093
[45] Date of Patent: Mar. 29, 1988

[54] REMOTE CONTROLLED CATHETER HAVING A MICRO-BALLOON

[75] Inventors: Philippe Bonello, Grand-Saconnex; Maurice Jeanmonod, Meyrin, both of Switzerland

[73] Assignee: Sarcem S.A., Meyrin, Switzerland

[21] Appl. No.: 929,082

[22] Filed: Nov. 10, 1986

[30] Foreign Application Priority Data

Nov. 21, 1985 [CH] Switzerland ............... 04961/85

[51] Int. Cl.$^4$ ............................................. A61M 25/00
[52] U.S. Cl. ............................................ 604/95; 604/96; 128/348.1
[58] Field of Search .................. 604/95–103; 128/344, 348.1

[56] References Cited

U.S. PATENT DOCUMENTS

| | | | |
|---|---|---|---|
| 3,467,101 | 9/1969 | Fogarty et al. | 128/348.1 |
| 3,670,729 | 6/1972 | Bennett et al. | 604/164 X |
| 4,150,676 | 4/1979 | Jackson | 128/207.15 |
| 4,215,703 | 8/1980 | Willson | 128/772 |
| 4,456,017 | 6/1984 | Miles | 128/772 |
| 4,561,439 | 12/1985 | Bishop et al. | 128/348.1 |
| 4,586,923 | 5/1986 | Gould et al. | 604/95 |
| 4,597,755 | 1/1986 | Samson et al. | 604/95 |
| 4,650,467 | 3/1987 | Bonello et al. | 128/348.1 X |

FOREIGN PATENT DOCUMENTS

| | | |
|---|---|---|
| 0161045 | 11/1985 | European Pat. Off. |
| 2954391 | 10/1979 | Fed. Rep. of Germany . |
| 372096 | 3/1907 | France . |
| 1278965 | 11/1961 | France . |
| 4327695 | 11/1968 | Japan ............... 604/95 |
| 2054385 | 2/1981 | United Kingdom . |
| 2127294 | 4/1984 | United Kingdom . |

Primary Examiner—Dalton L. Truluck
Attorney, Agent, or Firm—Young & Thompson

[57] ABSTRACT

A remote controlled catheter with micro-balloon, having a head constituted by a cylindrical coil spring (2) having separated coils covered by a micro-balloon (10) and mounted coaxially at the end of a tube (1). The spring can be bent at will in order to facilitate its introduction along arteries. The user pulls on the rear of a flexible pulling member (5) the forward end of which is fastened to the upper part of the head eccentrically of the axis of the head, this element (5) passing within the tube (1). To inflate the balloon (10), fluid is introduced through a channel (11), through the tube (1), the base of the balloon (10) being fixed to the tube (1) in a sealed manner. To inject a contrast liquid within the arterial channel, this liquid is introduced by a channel (12) communicating with the space between the tube (1) and the covering (9) and is expelled through two openings (13 and 14), this latter operation being possible thanks to the fact that one of the ends of the covering (9) is sealed to the frame member (6), whereas the other end is also sealed but on the tube (1).

3 Claims, 3 Drawing Figures

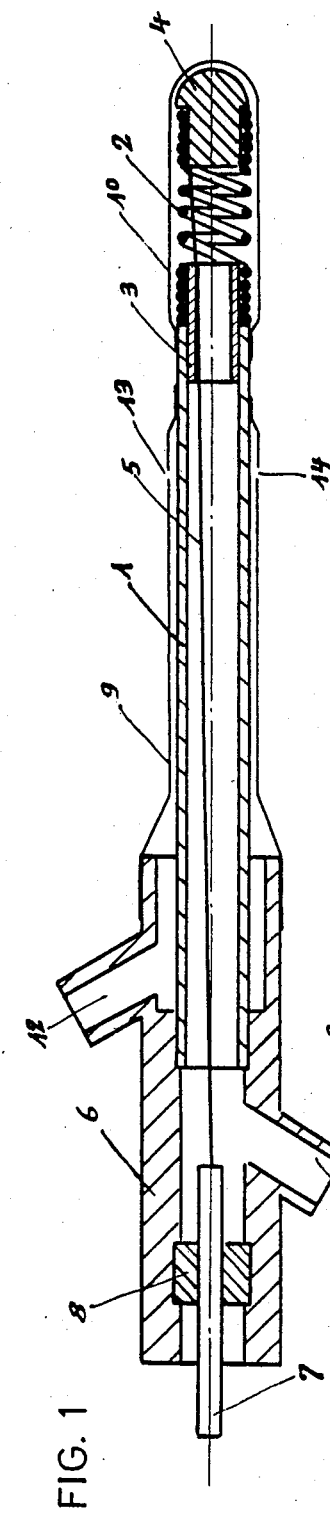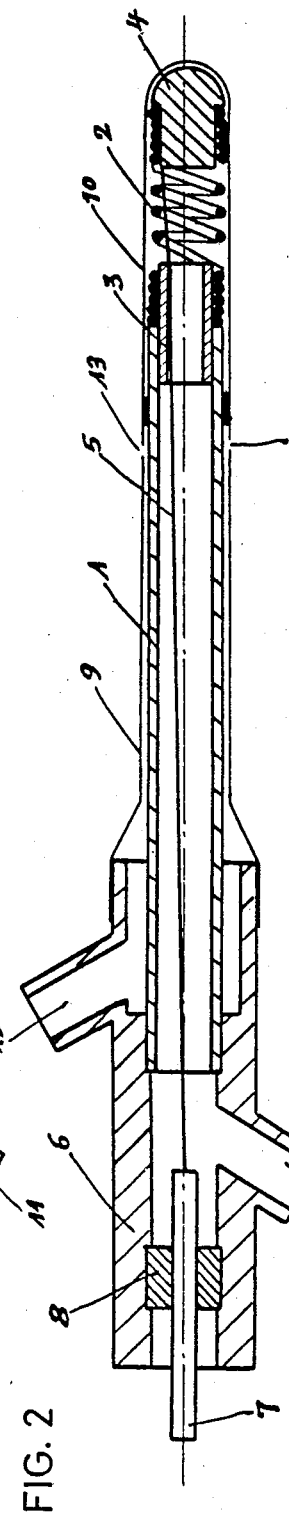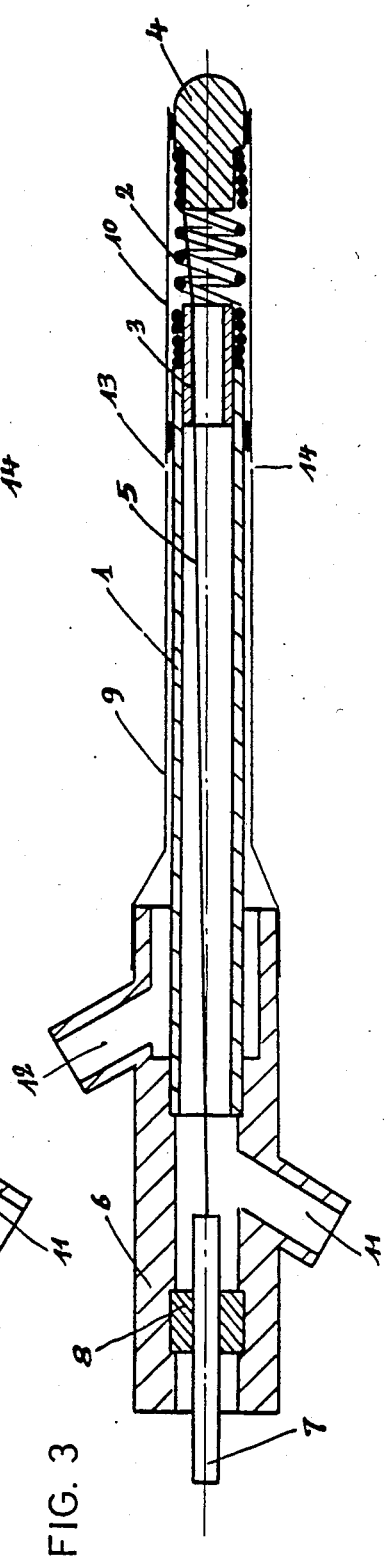

REMOTE CONTROLLED CATHETER HAVING A MICRO-BALLOON

The present invention has for its object a remote controlled catheter having a micro-balloon, the main uses of which are in the field of treatment of cardio-vascular disease at the level of the coronary vessels.

If the treatment of the narrowings of the calibre of the arteries or treatment of the stenosis is currently made by a method of dilatation by means of a catheter with an inflatable balloon, it is not always simple to place the said balloon through the multiple circulatory ramifications inside the stenosis, an operation which is of course the more difficult the greater is the narrowing. For certain stenosis particularly, and due to the fact that the arterial channel is reduced to very small dimensions, it is not possible to use the traditional catheter having a much too great diameter. The present invention has precisely for its object a catheter having an inflatable balloon of very small diameter the bending of the extremity of which can be remotely modified at will and this at any moment during the surgical intervention.

FIG. 1 shows a cross-section of the principle of the catheter, the tubular covering and the balloon being two distinct elements the one from the other.

FIG. 2 shows the catheter the tubular covering of which and the balloon of which are integral.

FIG. 3 shows the catheter in one or the other of its two above main variants, but the end of the part of which forming the balloon is fixed in a sealed manner on the end piece.

The remote controlled catheter having a micro-balloon shown in the drawing comprises a tube 1 at the end of which a head of the catheter is mounted coaxially, said head being composed of a cylindrical coil spring 2, the base of which is fitted onto a pierced part 3 itself partly driven into the tube 1, an end piece 4, the shank of which is fitted on the other end of the cylindrical coil spring 2, and a flexible pulling element 5, the point of fixation of which to the end piece 4 is eccentric with respect to the axis of the latter. Furthermore, we find also a frame element 6 fixed in a sealed manner on the tube 1, a partly cylindrical portion 7 to which is fixed the flexible pulling member 5, an o-ring 8 ensuring the seal between the frame element 6 and the cylindrical part 7, a tubular covering 9, and an inflatable balloon 10.

In order to direct the end or head of the catheter which is covered by its inflatable balloon 10 as shown in FIG. 1 into the inlet of one or the other of the circulatory ramifications and then within the zones to be treated, the user has three degrees of freedom, that is to go back and forth with the whole assembly and therefore with the head, the rotation of the whole assembly on itself in one or the other direction with respect to its axis, and the inclination or the straightening of the head, the last function being possible thanks to the backward pulling force against the resilient action of the cylindrical coil spring 2. The user can manipulate the partly cylindrical piece 7 and therefore the flexible pulling member 5 enclosed by the tube 1, the partly cylindrical part 7 being directly manually seizable by its rear end or attached by this same end to a classical non represented mechanism of the micro-metric type for example.

As to the inflatable balloon 10, the fluid under pressure is introduced through the channel 11 of the frame element 6 to enter to the balloon 10 through the tube 1, the base of the balloon 10 being fixed onto the tube 1 in a sealed manner.

Contrast liquid can be introduced within the circulatory ramification considered in order to trace for a radioscopic examination. For that, the contrast liquid is injected through the channel 12 of the frame element 6 filling the space between the tube 1 and the tubular covering 9 and is discharged through the holes 13 and 14 provided in said covering, this operation being possible thanks to the fact that one of the ends of the tubular covering 9 is liquid-tightly fixed on the frame element 6 whereas the other end is liquid-tightly fixed on the tube 1.

We claim:

1. A remote controlled catheter comprising a frame element having fluid passages therethrough, a tube supported by the frame element and in fluid communication therewith, said tube extending forwardly from the frame element, a tubular covering surrounding the tube and sealed at its rear end to the frame element and sealed at its forward end to a forward end portion of the tube, means for injecting liquid through the frame element and between the tube and the tubular covering, the tubular covering being laterally pierced to permit said liquid to escape from the catheter, a coil spring having spaced coils supported on the forward end of the tube and extending forwardly of the tube, a flexible pulling member connected to the coil spring forwardly of the forward end of the tube and extending through the tube and frame element, means supported within the frame element for adjustably exerting tension of the flexible pulling member thereby to deflect the spring laterally, an inflatable micro-balloon sealed to the forward end of the tube and surrounding the spring, and means for applying a fluid under pressure through one of the passages in the frame element and the tube and out the forward end of the tube into the micro-balloon to inflate the micro-balloon.

2. A catheter as claimed in claim 1, and an end piece spaced forwardly of the forward end of the tube, the forward end of the coil spring surrounding the end piece and securing the forward end of the flexible pulling member between the spring and the end piece.

3. A catheter as claimed in claim 1, in which the tubular covering and the micro-balloon are of one-piece construction, said one-piece construction being sealed to said forward end portion of the tube in such a way as to seal the laterally-pierced portion of the tubular covering from the interior of the micro-balloon.

* * * * *